United States Patent [19]

Mori et al.

[11] 4,376,131

[45] Mar. 8, 1983

[54] METHOD FOR CONTROLLING THE HEATING OF FOOD STUFF

[75] Inventors: Keijiro Mori, Nara; Shigeru Kusunoki, Yamatokoriyama; Kazunari Nishii, Yamatokoriyama; Tomotaka Nobue, Yamatokoriyama, all of Japan; Takato Kanazawa, deceased, late of Nara, Japan, by Kyoko Kanazawa, administratrix

[73] Assignee: Matsushita Electric Industrial Co., Ltd., Osaka, Japan

[21] Appl. No.: 183,582

[22] Filed: Sep. 2, 1980

[30] Foreign Application Priority Data

Sep. 7, 1979 [JP] Japan .................................. 54-115512

[51] Int. Cl.³ ............................................. G01N 33/02
[52] U.S. Cl. ..................................... 426/231; 99/325; 219/10.55 M; 426/241; 426/523
[58] Field of Search ............... 426/241, 231, 233, 243, 426/523; 219/10.55 M, 10.55 B, 10.55 E, 10.55 R; 99/325

[56] References Cited

U.S. PATENT DOCUMENTS 4,080,564  3/1978  Nitta et al. .................. 219/10.55 B
4,097,707  6/1978  Kobayashi et al. ................... 99/325
4,181,744  1/1980  Buck ..................................... 426/523

*Primary Examiner*—Raymond N. Jones
*Assistant Examiner*—George C. Yeung
*Attorney, Agent, or Firm*—Stevens, Davis, Miller & Mosher

[57] ABSTRACT

A food heating method and apparatus are disclosed in which a heating time length suitable to the food to be cooked is determined by automatically detecting a change in humidity or concentration of the vapor or gas respectively liberated from the food. The initial temperature of the food is measured, and an additional heating time length is calculated from the measured initial temperature and the heating time length required before the detection of the humidity or gas concentration as the case may be, thus determining a total heating time length for properly cooking up the food.

6 Claims, 9 Drawing Figures

METHOD FOR CONTROLLING THE HEATING OF FOOD STUFF

BACKGROUND OF THE INVENTION

The present invention relates to a method of heating food and a food heating apparatus.

In conventional cooking apparatus or ovens utilizing humidity sensing, for example, known from U.S. Pat. No. 4,097,707 issued June 27, 1978, the time length $\tau_o$ from the start of heating the food to the boiling of the food is measured, and from the time point when the food begins to boil, the food is further heated for a time length which is obtained by multiplying the time $\tau_o$ by a specific constant K depending on the type of food and the desired finished condition until the food is completely cooked. The amount of heat required before the cooking of the food is finished as desired is considered to be expressed by the equation below.

$$Q = n \cdot C \cdot (Tv - Ti) + m \cdot B \quad (1)$$

where
C: specific heat of the food,
m: quantity of the food,
Tv: temperature at which the water in the food begins to boil,
Ti: initial temperature of the food, and
B: a value specific to the food or the value dependent on the amount of heat associated with the change in quality (or degeneration) and the latent heat of evaporation.

The value Q is given as the product of the microwave power p and the total heating time of the food $\tau$, namely, $Q = p \cdot \tau$. Thus, the total heating time of the food is expressed as $$\tau = \frac{m \cdot C}{p}(Tv - Ti) + \frac{m}{p} \cdot B \quad (2)$$

The first term of the right side of this equation represents the time length from the starting of heating the food to the boiling of the water in the food, and the second term thereof is considered to represent the time from the start of boiling of the food to the properly cooked up state of the food. Therefore, the equation (2) may be rewritten as $$\tau = \tau_o + K\tau_o$$
$$\text{where } \tau_o = \frac{m \cdot C}{p}(Tv - Ti) \quad (3)$$
$$K = \frac{B}{C(Tv - Ti)}$$

In the conventional cooking ovens using the detection of humidity, the initial temperature of the food Ti in equation (3) above is assumed to be about 20° C. so that K is considered as a constant, with the result that the food heating time is controlled by equation (3).

The food to be heated for cooking, however, includes that which has been left to stand at a considerably high room temperature, that just taken out of the refrigerator, and frozen food, etc., which vary greatly from one another in the initial temperature immediately before being heated. The value K for such a wide range of food is not constant but greatly varied. In the prior art cooking ovens wherein the value K is assumed to be constant, food sometimes failed to be finished satisfactorily on account of the great variety of the initial temperature of the food to be cooked and the resulting wrong setting for the total heating time.

In a method of food heating control proposed to obviate this disadvantage, the food is heated slowly at low output or heating and suspension of heating of the food are alternated so that the internal temperature of the food is approximated to the surface temperature thereof, and under this condition, the time point when the surface temperature reaches a predetermined set value is detected by an infrared detector. From this time point of detection, the food is further heated for a time length obtained by multiplying the constant K specific to the food by a time length from the above-mentioned time point of detection to the time point of humidity detection when the humidity increases by violent generation of vapor, thus cooking the food.

The set value of the surface temperature is the initial temperature Ti in equations (1), (2) and (3) above. Thus the value K in equation (3) is also required to be determined anew by experiments. Assume, for instance, that the new initial temperature, namely, the set value is 50° C., the heating time from the start of heating to the time point of violent generation of vapor from the food when the humidity is detected is $\tau_o'$, and the heating time from humidity detection time to the time point when the food is cooked up properly is $\tau_h'$. Then the new constant K is given as $\tau_h'/\tau_o'$ as in the case of equation (3). In this method, the set value of initial temperature is required to be varied with food and determined by experiments, thereby complicating the cooking procedures.

Another shortcoming of this method is that the fact that the food temperature has reached the set value is detected by reference to the surface temperature thereof, and therefore in order to avoid a great error between the detected surface temperature and the internal temperature of the food being heated, the food is required to be heated sufficiently slowly or the heating and suspension of heating are required to be alternated thereby to attain the internal temperature as near to the surface temperature as possible, resulting in an excessively long cooking time.

Another proposed heating control method is such that the initial temperature of the food is measured and the food is heated first to a predetermined set value of the surface temperature thereof. The food is then further heated for a time length obtained by multiplying the heating time required for the food surface temperature to reach the set value from the start of heating, by a multiplicator calculated from the food initial temperature, the set value, a factor specific to the food to be cooked, the specific heat of the food and the microwave absorption rate of the food, thus cooking the food. This method also has the disadvantage that unless the food is heated slowly up to the predetermined set value of the surface temperature, there occurs a great difference between the surface temperature and the internal temperature of the food, so that the surface temperature fails to represent the food temperature as a set value, and therefore the total heating time cannot be determined properly. As a result, it takes a long time to attain a surface temperature near to the internal temperature of the food.

SUMMARY OF THE INVENTION

Accordingly, it is the object of the present invention to provide a cooking oven in which, in order to obviate the above-mentioned disadvantages of the prior art, the initial temperature of the food considered to have the same internal and surface temperature before cooking is measured by a food temperature measuring instrument on the one hand and the time point when the humidity rises by the violent liberation of vapor from the food is detected by a humidity sensor or detector on the other hand.

The cooking oven according to the present invention has the advantages mentioned below.

(1) Unlike the conventional or proposed methods in which the heating time length from the heating start to detection of humidity is used to determine the subsequent heating time length, such a subsequent heating time length is determined on the basis of the initial temperature of the food measured at the time of heating start and the time length from the heating start to humidity detection. Therefore, the error in determination of the heating time which otherwise might be caused by the variations in the initial temperature of the food is eliminated, thus making it possible to determine the food heating time length for properly cooking the food without being substantially affected by the initial temperature of the food including frozen food.

(2) As compared with the method in which the food is slowly heated until the surface temperature reaches a predetermined setting specific to the particular food and it is further heated from the time of humidity detection for a time length obtained by multiplying the time before humidity detection by a constant specific to the particular food, or as compared with the method in which the initial temperature of the food is measured and the time length required for the surface temperature of the food started to be heated to reach a predetermined set value is used to calculate the constant K, the present invention is such that the surface temperature in proximity to the internal temperature of the food while being heated is not required to be detected, so that the food can be heated more rapidly, thus shortening the total heating time required before the food is properly cooked.

(3) In view of the fact that the food temperature is measured only immediately before being heated, it is possible to provide a mechanism for covering the optical system of the temperature measuring instrument. Thus the cooking oven is prevented from being contaminated by juice or fat scattered out of the food, thereby eliminating the requirement of a complicated means for preventing the contamination of the instrument.

(4) In cooking the food, it is sufficient to designate the type of food, namely, a factor specific to the particular food involving the specific heat, microwave absorption rate latent heat and the temperature when the food begins to boil, thus making possible an automatic cooking operation without being substantially affected by the quantity of the food or the heating output but by automatically measuring the food initial temperature and the time length from the heating start to the humidity detection.

DESCRIPTION OF THE PREFERRED EMBODIMENTS

As embodiment of the present invention will be described below with reference to FIGS. 1 to 9.

Figure 1:
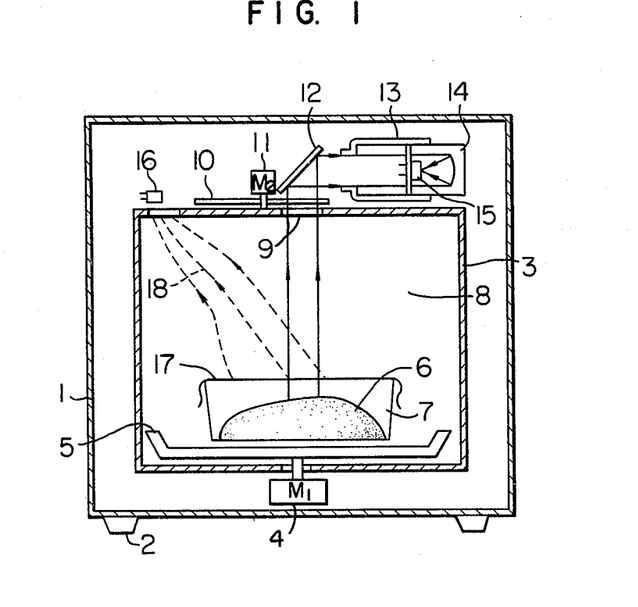
FIG. 1 is a diagram showing a construction of a food heating control apparatus (a cooking oven) embodying the present invention.

A cooking oven according to the present invention is shown in FIG. 1 in which a heat source is not shown.

Reference numeral 1 shows a housing, numeral 2 legs, numeral 3 a wall of the heating chamber, numeral 4 a motor for rotating a food pan 5, numeral 6 the food, and numeral 7 a dish in which the food is placed. The heating chamber is designated by numeral 8. Numeral 9 shows an opening formed at the central part of the ceiling of the heating chamber wall 3. Numeral 10 shows a chopper blade, numeral 11 a chopper motor, numeral 12 a reflector, numeral 13 a view field limiting hood, and numeral 14 a mirror assembly including a concave reflector. Numeral 15 shows a temperature measuring instrument (in the case illustrated, an infrared temperature measuring instrument). Numeral 16 shows a humidity sensor, numeral 17 a wrapping sheet for covering the dish 7. Numeral 18 is a water vapor flow liberated from the food through the sheet 17, which water vapor flow changes the humidity which in turn is detected by the humidity sensor 16.

Figure 2:
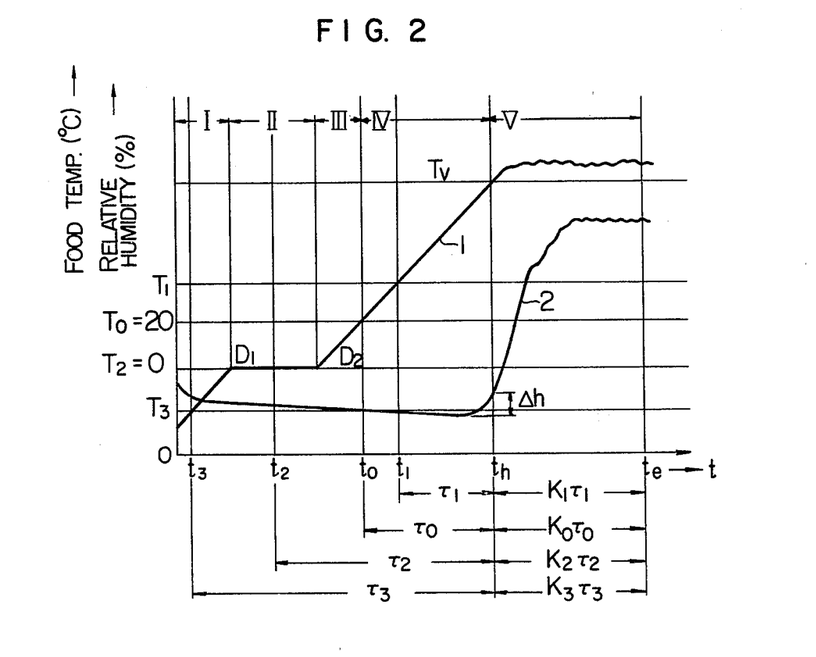
FIG. 2 shows a temperature curve and a relative humidity curve changing with the heating of the food according to the present invention.

The graph of FIG. 2 shows an example of change in relative humidity at an exhaust path outside the oven and the food temperature changing with the progress of heating of the cooking oven according to the present invention.

In the graph, the curve 1 represents the change in temperature with respect to the heating time in the case where the frozen food is heated up to the final finished condition, and the curve 2 a similar change in humidity.

Assume that the food of initial temperature $T_1$ is heated from the time point $t_1$. As shown in curve 2, little vapor is liberated from the food in the initial stage of heating, so that the relative humidity decreases with the rise in temperature of the inside of the oven. With the increase in the amount of vapor liberated, the relative humidity reaches a minimum level wherefrom it turns upward. At the time point $t_h$ when the relative humidity increases by a threshold value $\Delta h$ from the minimum value, a change occurs in the cooking condition of the food so conspicuously that the food begins to boil and the temperature thereof reaches about 92° C. to 97° C.

At this stage, the time point $t_h$ when the relative humidity increases is detected. The time length $\tau_1$ from the start of heating of the food to the time point $t_h$ is measured, and the factor $K_1$ is determined by the method of calculation described later. Thus the product $K_1 \cdot \tau_1$ of the time $\tau_1$ and the factor $K_1$ is used as a proper heating time.

If the food of the initial temperature $T_2$ ($=0°$ C.) is heated from the time point $t_2$, heat of fusion is required for changing the ice contained in the food into water and therefore the temperature does not increase before a certain time point (before the time point $D_2$ in the illustrated case). After this state, the temperature begins to increase and reaches $T_0$ ($=20°$ C.) at time point $t_0$ and passing the temperature $T_1$, the time point $t_h$ when the relative humidity increases is detected. In this case, the time length $\tau_2$ from the heating start point $t_2$ to the time point $t_h$ is measured, so that the factor $K_2$ is calculated by the method described later and the product $K_2 \cdot \tau_2$ thereof is used as a proper heating time length.

In similar fashion, assume that the food of the initial temperature $T_3$ (which is lower than $0°$ C.) is started to be heated at the time point $t_3$. At the time point $t_2$ soon after, the melting point ($=0°$ C.) is reached when the ice content in the food is transformed into water. Around this temperature, the heat of fusion of ice is required and therefore the temperature fails to increase for a certain period of time (from the time point $D_1$ to $D_2$ in the illustrated case). After this time point, the temperature continues to rise as in the previous case, so that the time point $t_h$ when the relative humidity increases is detected. The time length $\tau_3$ from the heating start time point $t_3$ to the time point $t_h$ is measured, and the factor $K_3$ is determined by the method of calculation described later, so that the product $K_3 \cdot \tau_3$ thereof is used as a proper heating time length.

The reason for which a proper heating time length is determined by this method of calculation will be described with reference to FIG. 2.

In the case of a microwave oven used as the cooking oven, the amount of heat required for the food of the initial temperature of lower than $0°$ C. to be cooked up properly may be expressed by the equation below.

$$p \cdot \tau = m \cdot Co \cdot (-Toi) + m \cdot Bo + m \cdot C(20 - Ti) + m \cdot C(Tv - 20) + m \cdot B \quad (4)$$

where
- p: microwave power,
- $\tau$: total heating time required before the food is cooked up properly,
- m: quantity of the food,
- C: specific heat of the food,
- Co: specific heat of the frozen food and a value thereof corrected by the microwave absorption rate under frozen condition,
- B: value specific to the food associated with the change in food quality and the latent heat of evaporation,
- Bo: heat of fusion of the food, which is 0 in the case of the food higher than $0°$ C. in temperature,
- Tv: temperature at which the food begins to boil,
- Ti: initial temperature of the food, which is 0 i the case of the food lower than $0°$ C. in temperature.
- Toi: the initial temperature of the food, which takes a negative value for the food lower than $0°$ C. and 0 for the food higher than $0°$ C.

In this equation, it is assumed that the amount of water evaporation is much smaller than m.

In equation (4) above, the first term of the right side represents the sensible heat, the second term thereof the heat of fusion, the third term thereof the sensible heat up to the temperature of $20°$ C., the fourth term thereof the sensible heat for higher than $20°$ C., and the fifth term thereof the evaporation heat and the amount of heat required for the food to change in quality. From equation (4), the total food heating time is given as $$\tau = \frac{m}{p} \cdot Co \cdot (-Toi) + \frac{m}{p} \cdot Bo + \frac{m}{p} \cdot C(20 - Ti) + \quad (5)$$

$$\frac{m}{p} \cdot C(Tv - 20) + \frac{m}{p} \cdot B$$

The temperature change which occurs when the frozen food is cooked by being heated up to a properly finished condition is shown in five stages in FIG. 2. Each stage in this drawing corresponds to each term in equation (5). Specifically, the first term in equation (5) corresponding to the region I shows the time for the food to be cooked at temperatures lower than $0°$ C., the second term corresponding to region II shows the time required for the food to be cooked at $0°$ C., and the third term shows the time corresponding to the region III shows the time required for the food to be cooked at temperatures from $0°$ C. to $20°$ C. Further, the fourth term corresponding to the region IV shows the time required for the food to be cooked at the temperatures from $20°$ C. to Tv $°$C. The fifth term shows the time required for the food to be cooked up properly from the temperature of Tv $°$C. and corresponds to the region V.

The values $\tau_0$ and $K_0$ below are substituted into the equation (5).

$$\left. \begin{array}{l} \tau_o = \dfrac{m}{p} \cdot C \cdot (Tv - 20) \\ K_o = \dfrac{B}{C(Tv - 20)} \end{array} \right\} \quad (6)$$

Then, the equation (5) is expressed as shown below.

First, in the case of the food having the initial temperature higher than $0°$ C., namely, in the cases of the regions III and IV, $$\left. \begin{array}{l} \tau = \tau_1 + K_1 \cdot \tau_1 \\ \text{where } \tau_1 = \dfrac{m}{p} \cdot C(Tv - Ti) \\ K_1 = K_o \cdot \dfrac{\tau_o}{\tau_1} \\ \quad = K_o \cdot \dfrac{Tv - 20}{Tv - Ti} \end{array} \right\} \quad (7)$$

In the case of the food having the initial temperature of $0°$ C., namely, the region II, on the other hand, $$\left. \begin{array}{l} \tau = \tau_2 + K_2 \cdot \tau_2 \\ \text{where } \tau_2 = \dfrac{m}{p} \cdot \left( \dfrac{B_o}{2} + C \cdot Tv \right) \\ K_2 = \dfrac{\tau_o}{\tau_2} \\ \phantom{K_2} = K_o \cdot \dfrac{C \cdot (Tv - 20)}{\dfrac{B_o}{2} + C \cdot Tv} \end{array} \right\} \quad (8)$$

In the above equations, the value $B_0/2$ is associated with intermediate time point between the states lower and higher than the freezing point and is the result of taking into consideration the fact that the food condition at 0° C. has a margin and cannot be easily identified. This eliminates large error regardless of the process of fusion.

In the case of the frozen food having the initial temperature lower than 0° C., namely, the region I, $$\left. \begin{array}{l} \tau = \tau_3 + K_3 \cdot \tau_3 \\ \text{where } \tau_3 = \dfrac{m}{p} \cdot (Co\, Toi + Bo + C \cdot Tv) \\ K_3 = K_o \cdot \dfrac{\tau_o}{\tau_3} \\ \phantom{K_3} = K_o \cdot \dfrac{C(Tv - 20)}{Co \cdot Toi + Bo + C \cdot Tv} \end{array} \right\} \quad (9)$$

The total heating time length of the food having the initial temperature of 20° C. is experimentally determined from equation (5) as below, $$\left. \begin{array}{l} \tau = \tau_o + K_o \tau_o \\ \text{where } \tau_o = \dfrac{m}{p} \cdot C(Tv - 20) \\ K_o = \dfrac{B}{C(Tv - 20)} \end{array} \right\} \quad (6)'$$

The value $\tau_0$ can be measured as a heating time required before humidity detection, and the total heating time length $\tau$ is capable of being measured as a time length required for the food to be cooked up properly. Therefore, from equation (6)', the value $K_0$ is given as $$K_0 = (\tau - \tau_0)/\tau_0$$

This value may be considered to be a constant which can be determined experimentarily for each food item.

The first terms of equations (7), (8) and (9), namely, the heating time lengths $\tau_1$, $\tau_2$, and $\tau_3$ required from the initial temperature to the temperature $Tv$ at which the food begins to boil are divided respectively into the part inversely proportional to the microwave power $p$ and proportional to the quantity of food $m$, and the part dependent on the values C, Tv, Ti, Bo, Co and Toi. This latter part increases or decrease the heating time $\tau_1$, $\tau_2$ or $\tau_3$ depending on the region of the initial temperature of the food. After the lapse of the heating time $\tau_1$, $\tau_2$ or $\tau_3$, however all food reaches the temperature $Tv$ at which it begins to boil.

Regardless of the initial temperature of the food, the time lengths $\tau_1$, $\tau_2$ and $\tau_3$ required for the food from the heating start to the boiling point can be measured. On the other hand, the factors $K_1$, $K_2$ and $K_3$ dependent on the constant $K_0$ experimentarily obtained, the values $Tv$, C, Bo and Co determined for each food as well as the measured values of the initial temperature $T_1$ or $Toi$ are already calculated. The heating time lengths $K_1\tau_1$, $K_2\tau_2$ and $K_3\tau_3$ following the time point when the food begins to boil can be calculated from the factors $K_1$, $K_2$ and $K_3$ subjected to change and the time lengths $\tau_1$, $\tau_2$ and $\tau_3$ from the heating start to the time point when the final measured temperature is reached. Thus, without measuring the quantity $m$ of the food, the total heating time length is obtained. In this case, it is not necessary to determine the actual value of B specific to each food associated with the latent heat of evaporation and the quality change of the food but the value may be substituted by the constant $K_0$ specific to the food which can be obtained by experiment beforehand. The temperature $Tv$ when the food begins to boil is set at approximately 95° C. Most food is high in moisture content and therefore is considered to have a specific heat of 1.0 like water.

The heat of fusion of the food, on the other hand, may be considered to be 79.7 Cal/g like that of ice on the assumption that the food contains much water. Further, the specific heat of the frozen food, which contains much ice as a water content, may be safely considered to be 1.16 at 0° C., 1.11 at −20° C. and 0.84 at −80° C. like water. The microwave absorption rate of the frozen food, which is dependent on the temperature and different from that of the unfrozen food, is 0.13 to 0.17 for beef, 0.11 for green peas, 0.14 for minced pork, 0.08 for potato, 0.24 for spinach and 0.04 for pumpkin. The microwave absorption rate lowers in inverse proportion to the temperature of the food, and therefore it takes a longer time for the frozen food to rise in temperature. The value Co of 4.6 to 29.0 may be used for the above-listed food items.

Figure 3:
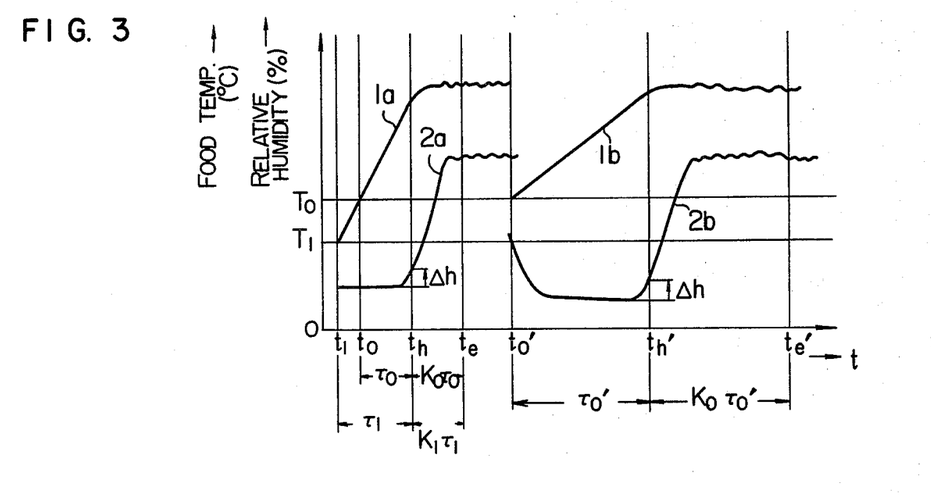
FIG. 3 shows a temperature curve and a relative humidity curve dependent on the quantity of the food to be cooked according to the present invention.

The graph of FIG. 3 shows another example of relative humidity in the exhaust path outside the oven and the food temperature changing with the progress of heating of the food in the cooking oven according to the present invention. The curves 1a and 2a in the graph show the changes in temperature and relative humidity respectively. It will be seen that the food having the initial temperature $To$ of 20° C. begins to be heated at the time point $t_0$, continues to be heated for the time length $\tau_0$ till the detection of humidity, and further continues to be heated for a time length obtained by multiplying the time length $\tau_0$ by the factor $K_0$, thus completing the cooking thereof.

It will also be seen that the same food having the initial temperature of $T_1$ is started to be heated at the time point $t_1$, further heated for the time period $\tau_1$ until the detection of humidity, and calculating the factor $K_1$ from the initial temperature and the like, further heated for the time length $K_1\tau_1$ thereby to cook it up to a proper condition.

The curves 1b and 2b similarly represent changes in temperature and relative humidity in the case of the food of the same type as that for the curves 1a and 2a but greater in quantity. The food having the initial temperature $To$ of 20° C. is started to be heated at the time point $t_0'$ and continues to be heated for the time length $\tau_0'$ until the detection of humidity, followed by further heating for the time length $K_0\tau_0'$ which is the product of the time length $\tau_0'$ and the factor $K_0$. In other words, the food is cooked up properly for the total heating time of $\tau_0' + K_0\tau_0'$. Naturally, the value $\tau_0'$ is longer than the time length $\tau_0$ in proportion to the food quantity involved.

Figure 4:
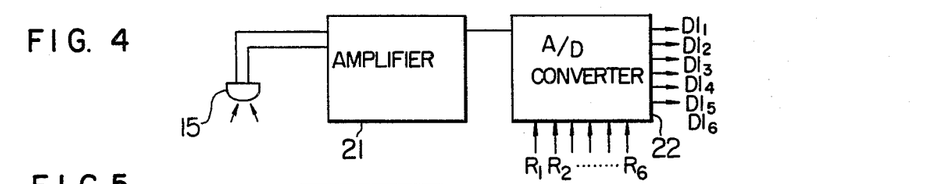
FIG. 4 is a diagram showing a configuration of means for temperature measurement of the cooking oven according to the present invention.

In FIG. 4, numeral 15 shows a temperature measuring instrument, numeral 21 an amplifier for amplifying the temperature signal produced from the temperature measuring instrument 15, and numeral 22 an analog-digital converter for converting the output of the amplifier 21 into a digital signal, which produces parallel digital signals $DI_1$, $DI_2$, $DI_3$, ..., $DI_6$ at the output terminals thereof. These parallel digital signals $DI_1$, $DI_2$, $DI_3$, ..., $DI_6$ are produced at the output terminals of the analog-digital converter 22 in response to the signals $R_1$, $R_2$, $R_3$, ..., $R_6$ representing the results of measurements of the initial temperature of the food taken immediately before being heated by the temperature measuring instrument (not shown).

Figure 5:
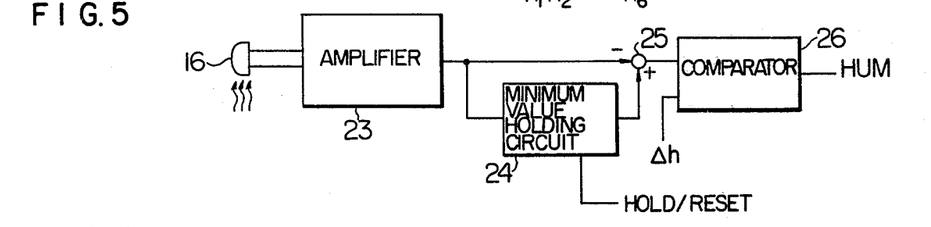
FIG. 5 shows a configuration of means for humidity detection of the cooking oven according to the present invention.

In FIG. 5, numeral 16 shows a humidity detector, numeral 23 an amplifier for amplifying the humidity signal, and numeral 24 a minimum value holding circuit for holding while updating a value smaller than the minimum of the output voltage of the amplifier 23. Numeral 25 shows a subtractor for subtracting the value at each moment of the output of the amplifier 23 from the minimum value held in the minimum value holding circuit 24. The output of the subtractor 25 is compared with the threshold value $\Delta h$ at the comparator 26. In the case where comparison shows that the output of the subtractor 25 is larger than the threshold value $\Delta h$, the comparator 26 detects the relative humidity due to the water vapor liberated from the food and produces a humidity detection signal HUM. A hold/reset signal is an input for restoring the starting condition by holding or erasing the holding voltage of the minimum value holding circuit 24.

Figure 6:
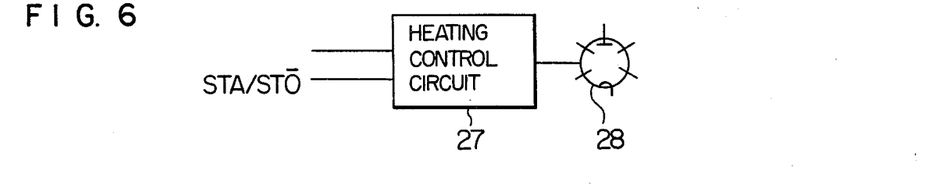
FIG. 6 is a diagram showing a configuration of heating control means of the cooking oven according to the present invention.

In FIG. 6, numeral 27 shows a heating control circuit for controlling the actuation and deactivation of the magnetron 28 in response to the magnetron start/stop signal $STA/\overline{STO}$.

Figure 7:
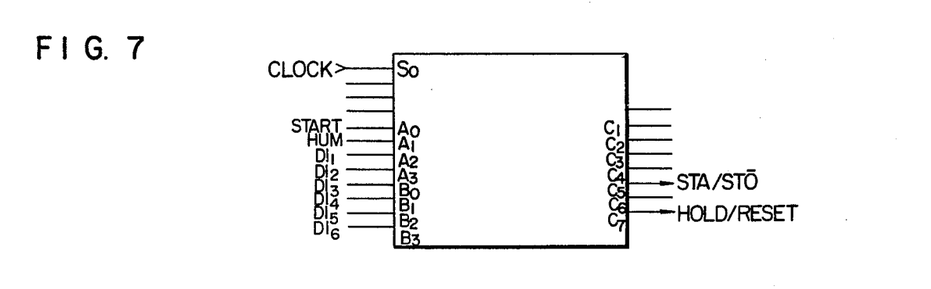
FIG. 7 is a diagram showing a control unit for the cooking oven according to the present invention.

FIG. 7 shows a control unit according to the present invention using an LSI chip. In this case, the LSI chip used is a general-purpose one of stored program type which is a microcomputer 200.

Reference characters $A_0$, $A_1$, $A_2$, $A_3$, $B_0$, $B_1$, $B_2$, $B_3$ and $S_0$ show input terminals, and $C_0$ to $C_9$ output terminals. The input terminals $A_0$ and $A_1$ are impressed with the heating start signal START and the humidity detection signal HUM respectively. The input terminals $A_2$, $A_3$, $B_0$, $B_1$, $B_2$ and $B_3$, on the other hand, are impressed with the parallel signals $DI_1$, $DI_2$, $DI_3$, ..., $DI_6$ which are the result of analog-digital conversion of the initial temperature.

The input terminal $S_0$ is impressed with clock pulses CLOCK (such as a commercial frequency) providing a time reference.

The magnetron start/stop signal $STA/\overline{STO}$ and the hold/reset signal HOLD/RESET for the minimum value holding circuit 24 are produced at the output terminals $C_5$ and $C_9$ respectively.

Figure 8:
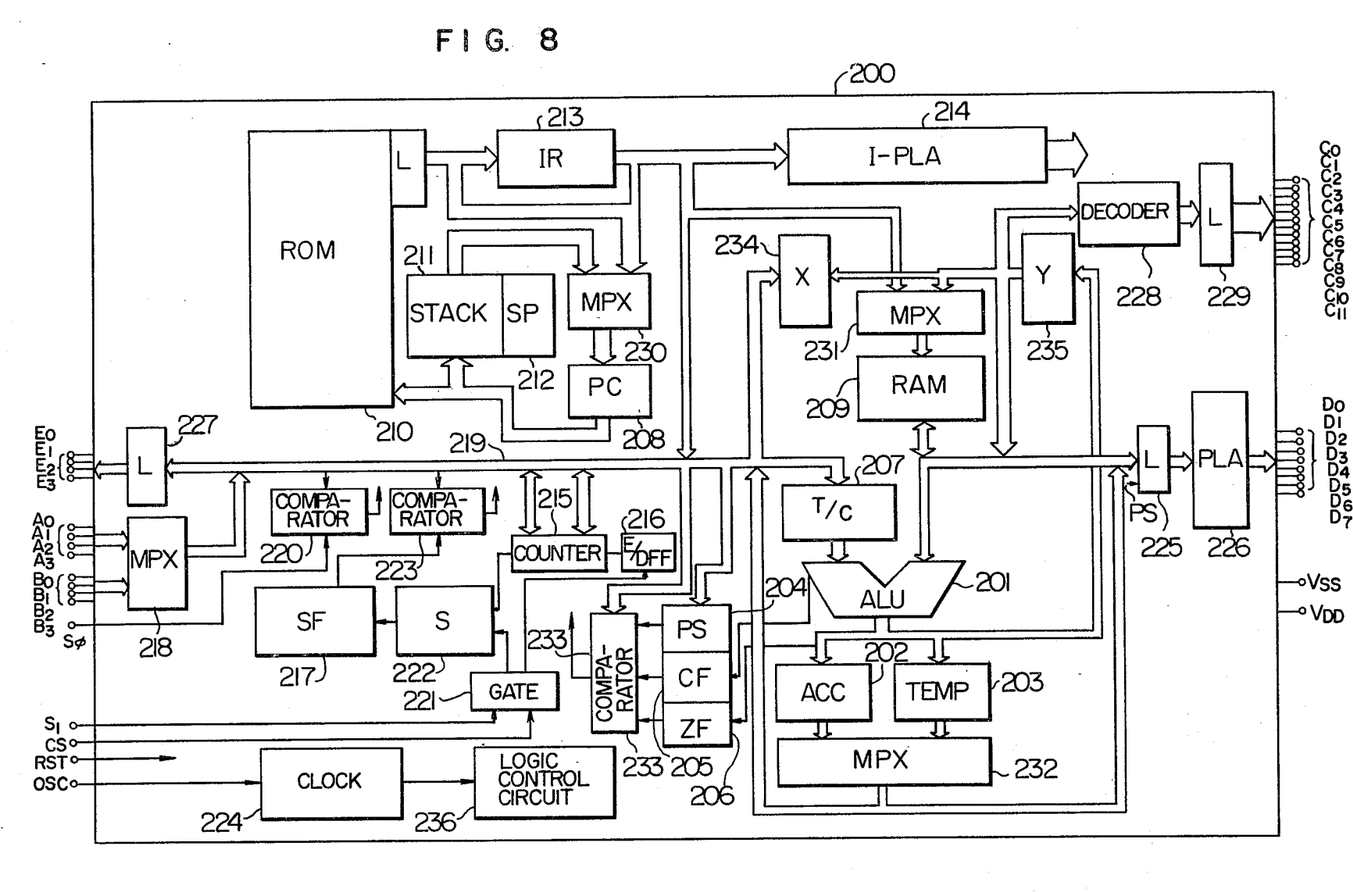
FIG. 8 shows a configuration of a microcomputer making up a part of the control unit.

A block diagram of the configuration of the microcomputer 200 is shown in FIG. 8. With reference to FIG. 8, the functions and the data processing program of the microcomputer 200 will be briefly explained.

A first function is a logic calculation which is attained by a logic calculation unit ALU 201, an accumulator ACC 202, a temporary register TEMP 203, a program status flag PS 204, a carry flag 205, a zero flag 206, a twos complement T/C 207 and 4-bit A and B buses for data transmission. The logic calculation section ALU 201 is capable of executing the operation of AND, OR, exclusive OR and addition. The twos complement T/C 207 is for calculating the complement of 2 for the data transmitted to ALU 201 and therefore ALU 201 is capable of executing the subtracting operation.

PS 204, CF 205 and ZF 206 show 1-bit flip-flops for storing the system conditions. The flip-flop PS 204 is a flag set or reset in response to a command. The flip-flops CF 205 and ZF 206 are used for various decisions in program execution in such a manner that the flip-flop ZF 206 is set or reset depending on whether or not the calculation result of the flip-flop CF 205 is zero, which is determined from the presence or absence of a carrier on the basis of the calculation result of the logic calculation unit ALU 201 or the like.

Symbols ACC 202 and TEMP 203 show 4-bit resisters for temporarily storing the input data and the calculation result of the logic calculation unit ALU 201.

A second function is data storage. This function is performed by a variable memory RAM 209, an X register 234 and a Y register 235. The addresses of the variable memory RAM 209 are designated by the X and Y registers so that the data stored in RAM 209 is capable of being transferred to the register ACC 202 or the like in response to a command.

A third function is to store and execute a program. This function is performed by a fixed memory ROM 210, a program counter PC 208, subroutine stack STACK 211 and a stack pointer SP 212. The fixed memory ROM 210 is for storing a program to be executed of a system which is written in 8-bit instruction words, and the program counter PC 208 comprising a binary counter is for designating the addresses of the fixed memory ROM 210. Thus with the counting up of the program counter PC 208, the program stored in the fixed memory ROM 210 is executed word by word. The subroutine stack STACK 211 is for storing the data of PC 208 in order to designate an address upon return from the subroutine. The stack pointer SP is for designating an address of a first return in execution of the subroutine in two levels.

A fourth function is that of decoding a command. This function is accomplished by an instruction register IR 213 and an instruction programmable logic array I-PLA 214. The instruction register IR 213 is for latching the 8-bit instruction words transferred from the fixed memory 210 while the instruction is being executed, and contains 8-bit data. The instruction programmable logic array I-PLA 214 performs the function of converting the 8-bit instruction words transferred from the fixed memory ROM 210 into a control signal, so that the 8-bit instruction words stored in the fixed memory 210 are converted sequentially into various control signals, which are transmitted to the other operating sections such as ALU, ACC and RAM, with the result the microcomputer operates on the basis of the program stored in the fixed memory ROM 210.

A fifth function is that of a counter. A counter 215 is an 8-bit binary counter, and is set or reset by a counter flip-flop E/DFF 216. After the counter 215 is rendered ready for counting operation by the flip-flop E/DFF 216, the input pulses from the input terminal $S_1$ are counted up, and when the pulses are counted up to the most significant bit MSB, the set flag SF 217 is set. Thus, by setting or resetting the flip-flop E/DFF 216 in response to a command from the fixed memory ROM 210 to see whether the set flag SF 217 is set or not, it is possible to count the number of the pulses from the input terminal $S_1$.

Also, the data in the counter 215 may be divided into the high-order 4-bits and the low-order 4-bits for direct transfer to the register ACC 202 or the like.

A sixth function is an input-output function. Input terminals include 4-bit parallel input terminals $A_0$ to $A_3$ and 4-bit parallel input terminals $B_0$ to $B_3$. These two sets of parallel inputs $A_0$ to $A_3$ and $B_0$ to $B_3$ may be selectively transferred to the register ACC 202 or the like by a multiplexer MPX 218 through a B bus 219. These inputs $A_0$ to $A_3$ and $B_0$ to $B_3$ are used for data input.

The other input terminals include input terminals $S_\phi$ and $S_1$. These input terminals are conveniently used for counting pulse signals or interruption without regard to the clock of the microcomputer. The high or low state of the input $S_\phi$ is determined by the comparator C 220. The input $S_1$ is applied to the counter 215 through the gate 221 or directly applied to the set flag SF 217 through a synchronizing circuit S 222 and compared at the comparator C 223. In this way, the input $S_1$ is used in similar fashion to the input $S_\phi$. Whether or not the input $S_1$ is to be applied to the counter 215 is determined by the input at the terminal CS.

The input terminal RST is used for holding the start (0 address) of the program stored in the fixed memory ROM 210 until the power supply for the microcomputer is established at the time of initial power throw-in, thus preventing any malfunction. Under this condition, all the output terminals are at $L_0$. The input terminal OSC is a terminal for connecting a capacitor and a resistor for determining the oscillation frequency of the built-in oscillator 224. Using the oscillation frequency of this oscillator as a clock, the logic control circuit 236 controls the internal operation of the microcomputer. Characters $V_{SS}$ and $V_{DD}$ show power terminals.

The output terminals are of three types. A first group of output terminals is an output terminal group D including the output terminals $D_0$ to $D_7$. When the data in the memory RAM 209 or the register ACC 202 and the flip-flop PS 204 are latched by the latch 225 and transferred to the programmable logic array PLA 226 as 5-bit data, the particular data of 5-bits are produced as parallel 8-bit data at the eight output terminals $D_0$ to $D_7$. Thus the output terminals $D_0$ to $D_7$ are suitable for display on a 7-segment display tube.

A second output terminal group E include output terminals $E_0$ to $E_3$ wherefrom 4-bit data are produced in parallel through the register ACC 202 or the fixed memory ROM 210. Numeral 227 shows a latch.

A third output terminal group C includes output terminals $C_0$ to $C_{11}$. These outputs C may be set or reset independently of each other. Specifically, when the Y register 235 designates a particular output terminal C to be set and issues an output command, the particular output terminal is latched by the latch 229 through the decoder 228 for producing an output. Thus various loads may be controlled by the output terminals C. Numerals 230, 231 and 232 show multiplexers and numeral 233 a comparator.

The foregoing is a brief description of the functions and data processing of the microcomputer shown in FIG. 8. The present invention includes an embodiment using such a microcomputer.

Figure 9:
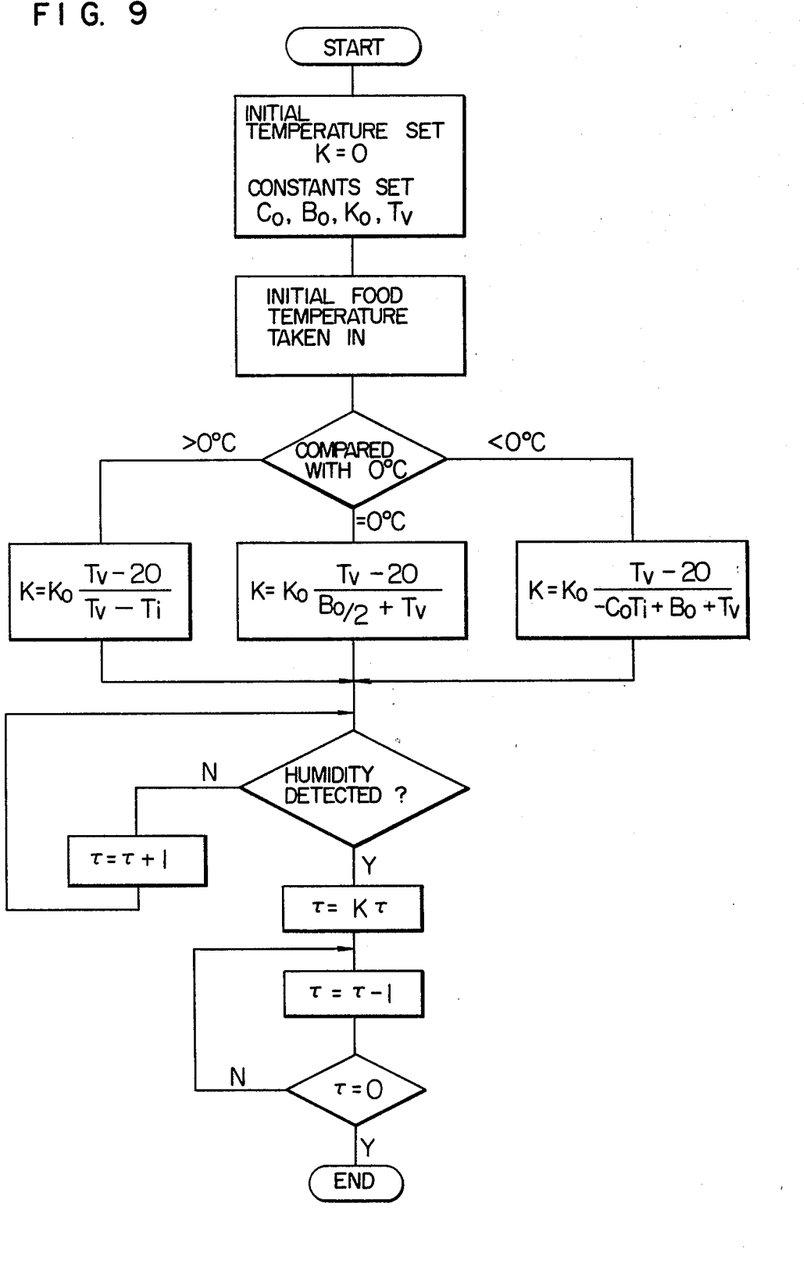
FIG. 9 is a flowchart schematically showing a heating control program of the microcomputer shown in FIG. 8.

A schematic flowchart of a heating control program of the microcomputer is shown in FIG. 9. The manner in which the operation of the cooking oven according to the present invention is controlled will be described below with reference to FIGS. 1 to 9.

The food is placed in the oven shown in FIG. 1 and is started to be heated. A heating start signal START is applied to the input terminal $A_0$ of the microcomputer shown in FIG. 7, thus starting the heating control. The temperature measuring instrument shown in FIG. 5 measures the initial temperature of the food, or alternatively, the food temperature is measured by another temperature measuring instrument before heating the food. A temperature measurement signal is converted into a digital signal at the analog-digital converter 22 and applied in the form of parallel digital signals to the input terminals $DI_1$, $DI_2$, $DI_3$, ..., $DI_6$. These signals are stored as the food initial temperature data in the RAM of the microcomputer.

When the relative humidity increases from the minimum value thereof and exceeds the threshold value $\Delta h$ with the progress of the heating of the food, the humidity detection signal HUM is produced from the comparator 26 shown in FIG. 5. This signal is applied to the input terminal $A_1$ of the microcomputer and stored therein as data.

The program executed by the program storage and execution functions of the microcomputer is shown in the flowchart of FIG. 9. In response to the heating start signal, the control process starts, so that the variable factor K is reduced to zero as initial setting, thus setting the constants Co, Bo, Ko and Tv.

The initial temperature Ti (including Toi) of the food is taken into the RAM in the manner mentioned above. After that, the initial temperature thus taken in is compared with "0° C.". If the initial temperature is higher than 0° C. (namely, the region III or IV shown in FIG. 2 is involved), the calculation $K=K_o(Tv-20)/(Tv-Ti)$ is made; if the initial temperature is equal to 0° C. (namely, when the region II shown in FIG. 2 is involved), the calculation $K=K_o(Tv-20)/(Bo/2+Tv)$ is made; and if the initial temperature is lower than 0° C. (namely, when the region I in FIG. 2 is involved), the calculation $K=K_o(Tv-20)/(-CoTi+Bo+Tv)$ is made. To simplify matters, the calculation of K in the regions II and I in FIG. 2 can employ C=1 (equations (8) and (9)).

From the time point when the heating is started to the time point $t_h$ of FIG. 2 when the humidity detection signal is stored and decision is made on whether or not the humidity is detected, the variable memory RAM increases the data stored therein from $\tau=0$ in the form of an increased number of clock pulses. When the decision is made that the humidity has been detected, the data $\tau$ in the RAM is multiplied by K. As a result, the time length $K\tau$ from the time points $t_h$ to $t_e$ shown in FIG. 2 is determined. This time value $K\tau$ is then reduced until the data in the RAM is reduced to "0". Specifically, at the time point $t_e$ when the decision is made that the data stored in the RAM is "0", the start/stop signal STA/$\overline{STO}$ is produced from the output terminal $C_5$ of the microcomputer. This signal is applied to the heating control circuit 27 in FIG. 6, so that the magnetron 28 is stopped, thus completing the cooking. The time $\tau$ and $K\tau$ are capable of being realized by applying the clock pulses CLOCK (such as a commercial frequency) providing a time reference at the input terminal So of the microcomputer and counting them within the RAM region.

In the aforementioned embodiment, the humidity is used to detect the time point $t_2$ when the temperature sharply increases by the vapor violently liberated from the food by the heating thereof. As an alternative method, the gas liberated from the food being heated may be used to detect a time point when the concentration of the gas increases, with equal effect.

What is claimed is:

1. A method for controlling the heating of a food stuff in a food heating apparatus which includes a high frequency oscillator, a food temperature measuring instrument, at least one of a humidity detector and a gas detector, and a control circuit for operating said oscillator, said controlling method comprising the steps of:

setting, depending on a type of said food stuff to be heated, a heating period coefficient ($K_o$) specific to said food stuff and corresponding to a predetermined reference initial temperature of the foof stuff, said heating period coefficient being stored in said control circuit, measuring, before heating, an initial temperature ($T_i$) of the food stuff by said food temperature measuring instrument;

starting the heating of the food stuff;

calculating a corrected heating period coefficient ($K$) as a function of at least said measured initial temperature ($T_i$) of the food stuff, said heating period coefficient ($K_o$), and said predetermined reference initial temperature;

heating the food stuff for a first time period ($\tau$) until a value detected by one of said humidity detector and said gas detector reaches a predetermined level from a minimum value;

counting said first time period ($\tau$) from the start of heating until said value detected by one of said humidity detector and said gas detector reaches the predetermined level; and, further heating the food stuff for an additional second time period ($K\tau$), following said first time period, which is obtained by multiplying said first time period ($\tau$) by said corrected heating period coefficient ($K$), whereby the heating time length for the food stuff is determined properly by eliminating errors due to differing initial temperatures of the food stuff.

2. A method of controlling heating of a food stuff according to claim 1 wherein said calculating step comprises the step of:

comparing said measured initial temperature ($T_i$) of the food stuff with a predetermined reference temperature to determine whether said food stuff is in a frozen condition or not;

and calculating the corrected heating period coefficient ($K$), when said food stuff is in the frozen condition, as a function of said measured initial temperature ($T_i$), said predetermined reference initial temperature, said present heating period coefficient ($K_o$) and a further coefficient ($B_o$) relating to the heat of fusion of said food stuff.

3. A method for controlling the heating of a food stuff according to claim 1, wherein said predetermined level is determined by forming a difference between said minimum value and said value detected by one of said humidity detector and said gas detector, said predetermined level being indicated when said difference exceeds a predetermined threshold value.

4. A method for controlling the heating of a food stuff according to claim 1 wherein said control circuit is a computer, and said computer stores said predetermined reference initial temperature and heating period coefficient $K_o$, starts said oscillator to heat the food stuff, calculates a corrected heating period coefficient ($K$), continues operation of said oscillator to heat the food stuff for said first time period ($\tau$), counts said first time period ($\tau$), and further continues to operate said oscillator to further heat a food stuff for said second time period.

5. A method for controlling the heating of a food stuff according to claim 1, wherein said food temperature measuring step includes measuring the temperature of the food and setting a value obtained by converting the result of said measuring step into digital form.

6. A method for controlling the heating of a food stuff according to claim 1, wherein the initial temperature $T_i$ of the food is measured by sensing infrared radiation radiated from the food.

* * * * *